(12) United States Patent
Morgan et al.

(10) Patent No.: US 7,029,900 B2
(45) Date of Patent: Apr. 18, 2006

(54) **TYPE II RESTRICTION ENDONUCLEASE BTGZI, OBTAINABLE FROM *BACILLUS THERMOGLUCOSIDASIUS* 36A AND A PROCESS FOR PRODUCING THE SAME**

(75) Inventors: Richard D. Morgan, Middleton, MA (US); Paul Walsh, Boston, MA (US)

(73) Assignee: New England Biolabs, Inc., Ipswich, MA (US)

( * ) Notice: Subject to any disclaimer, the term of this patent is extended or adjusted under 35 U.S.C. 154(b) by 312 days.

(21) Appl. No.: 10/617,361

(22) Filed: Jul. 10, 2003

(65) Prior Publication Data

US 2005/0233432 A1    Oct. 20, 2005

(51) Int. Cl.
*C12N 9/22*    (2006.01)

(52) U.S. Cl. ...................................... 435/199
(58) Field of Classification Search ...................... None
See application file for complete search history.

(56) References Cited

U.S. PATENT DOCUMENTS 5,200,333 A    4/1993    Wilson ..................... 435/172.3

OTHER PUBLICATIONS

Endow, et al., J. Mol. Biol. 112:521 (1977).
Waalwijk, et al. Nucleic Acids Res. 5:3231 (1978).
Gingeras and Brooks, Proc. Natl. Acad. Sci. USA 80:402 (1983).
Gingeras, et al., Nucl. Acids. Res. 5:4105 (1978).
Sanger, et al., Proc. Natl. Acad. Sci. 74:5463-5467 (1977).
Brown, et al., J. Mol. Biol. 140:143-148 (1980).
Matsudaira, et al. J. Biol. Chem. 262-10035-10038 (1987).
Looney, et al., Gene 80:193-208 (1989).
Waite-Rees, et al., J. Bacteriol. 173:5207-5219 (1991).

*Primary Examiner*—Charles L. Patterson, Jr.
(74) *Attorney, Agent, or Firm*—Gregory D. Williams; Harriet M. Strimpel

(57) ABSTRACT

In accordance with the present invention, there is provided a novel restriction endonuclease obtainable from *Bacillus thermoglucosidasius* 36A (NEB#1384), hereinafter referred to as "BtgZI", which endonuclease:

(1) recognizes the nucleotide sequence 5'-GCGATG-3' in a double-stranded DNA molecule as shown below,

```
5'-GCGATGNNNNNNNNNN↓-3'        (SEQ ID NO:9)

3'-CGCTACNNNNNNNNNNNNNN↑-5'
```

(wherein G represents guanine, C represents cytosine, A represents adenine, T represents thymine and N represents either G, C, A, or T);

(2) cleaves said sequence in the phosphodiester bonds between the 10th and the 11th nucleotides 3' to the recognition sequence in the 5'-GCGATG-3 strand of the DNA, and between the 14th and 15th nucleotides 5' to the recognition sequence in the complement stand, 5'-CATCGC-3', to produce a 4 base 5' extension; and (3) cleaves double-stranded pBR322 DNA to produce 3 fragments of 2892, 1181 and 288 base pairs.

3 Claims, 5 Drawing Sheets

BtgZI Figure 1: Agarose gel showing BtgZI cleavage of lambda, T7, pBR322 and PhiX174 DNAs.

BtgZI Figure 2 : Determination of the BtgZI cleavage site.

Figure 2A: Location of cleavage on 5'-CATCGC-3' strand.

A DNA (Sep-S3AI8.G10R) having a BtgZI site and a convenient primer was cut with BtgZI, yielding ends indicated by the arrows:

5'-..CGATGAGAATGCGATGTTGGTGGCCA↓AAAGCAATTATCC..-3'
    (SEQ ID NO:1)
3'-..GCTACTCTTACGCTACAACCACCGGTTTTC↑GTTAATAGG..-5'

The resulting cleaved DNA:
5'-..CGATGAGAATGCGATGTTGGTGGCCA-3' (SEQ ID NO:2)
3'-..GCTACTCTTACGCTACAACCACCGGTTTTC-5'

The template strand for dideoxy DNA sequencing extension:
3'-..GCTACTCTTACGCTACAACCACCGGTTTTC-5'

The primer is annealed and extended through the BtgZI site. When the reaction reaches the end of the molecule the Taq polymerase adds an extra A base.

5'-PRIMER-AGAATGCGATGTTGGTGGCCAAAAG(A)-3' (SEQ ID NO:3)
3'-..GCTACTCTTACGCTACAACCACCGGTTTTC-5'

Sequencing Profile of BtgZI cut Sep-S3AI8.G10R DNA (ABI377 Sequencer)

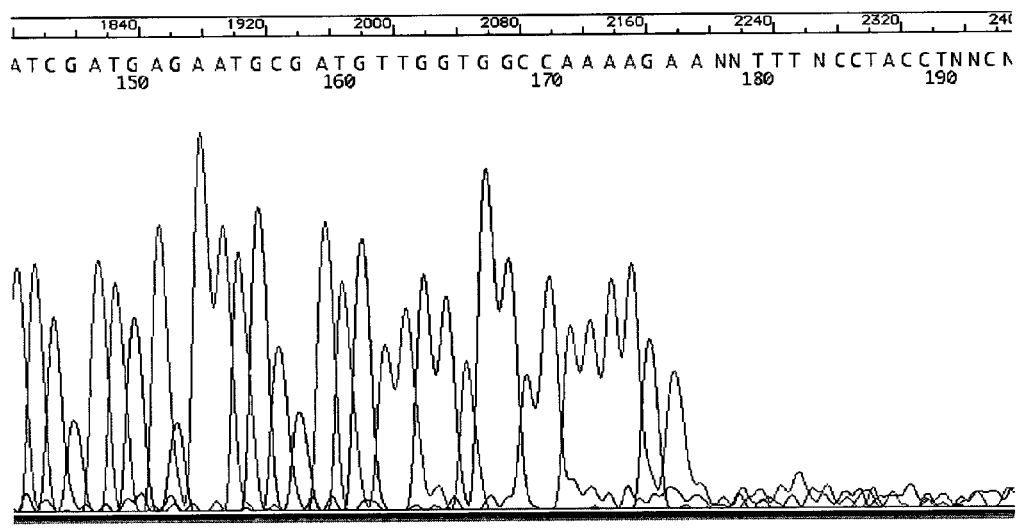

BtgZI Figure 2 : Determination of the BtgZI cleavage site.

Figure 2B: Location of cleavage on 5'-GCGATG-3' strand.

A DNA (Sep-S3AI8.G10L) having a BtgZI site and a convenient primer was cut with BtgZI, yielding ends indicated by the arrows:

5'-..TTCTTTCTGCGCGGTCAACT↓TTGTACCAATCATACATCGCCTGAG..-3'
    (SEQ ID NO:4)

3'-..AAGAAAGACGCGCCAGTTGAAACA↑TGGTTAGTATGTAGCGGACTC..-5'

The resulting cleaved DNA:
5'-..TTCTTTCTGCGCGGTCAACT (SEQ ID NO:5)
                              (5'-TTGTACCAATCATACATCGCCTGAG..-3')
                              (SEQ ID NO:6)
3'-..AAGAAAGACGCGCCAGTTGAAACA (3'-    TGGTTAGTATGTAGCGGACTC..-5')

The template strand for dideoxy DNA sequencing extension:
3'-..AAGAAAGACGCGCCAGTTGAAACA The primer is annealed and extended through the BtgZI site. When the reaction reaches the end of the molecule, the Taq polymerase adds an extra A base.

5'-PRIMER-> TTCTTTCTGCGCGGTCAACTTTGT(A)-3'  (SEQ ID NO:7)
3'-.........AAGAAAGACGCGCCAGTTGAAACA - 5'

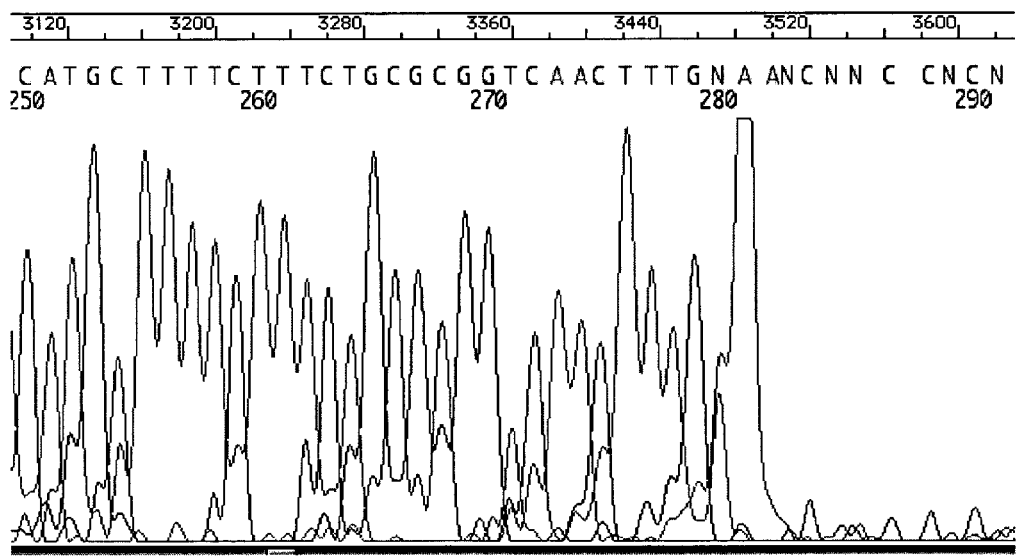

BtgZI Figure 3: SDS-PAGE gel of purified BtgZI endonuclease protein.
10 to 20% Tris-Tricine polyacrylamide gradient gel (Invitrogen-Novex), stained with Coomassie blue R-250
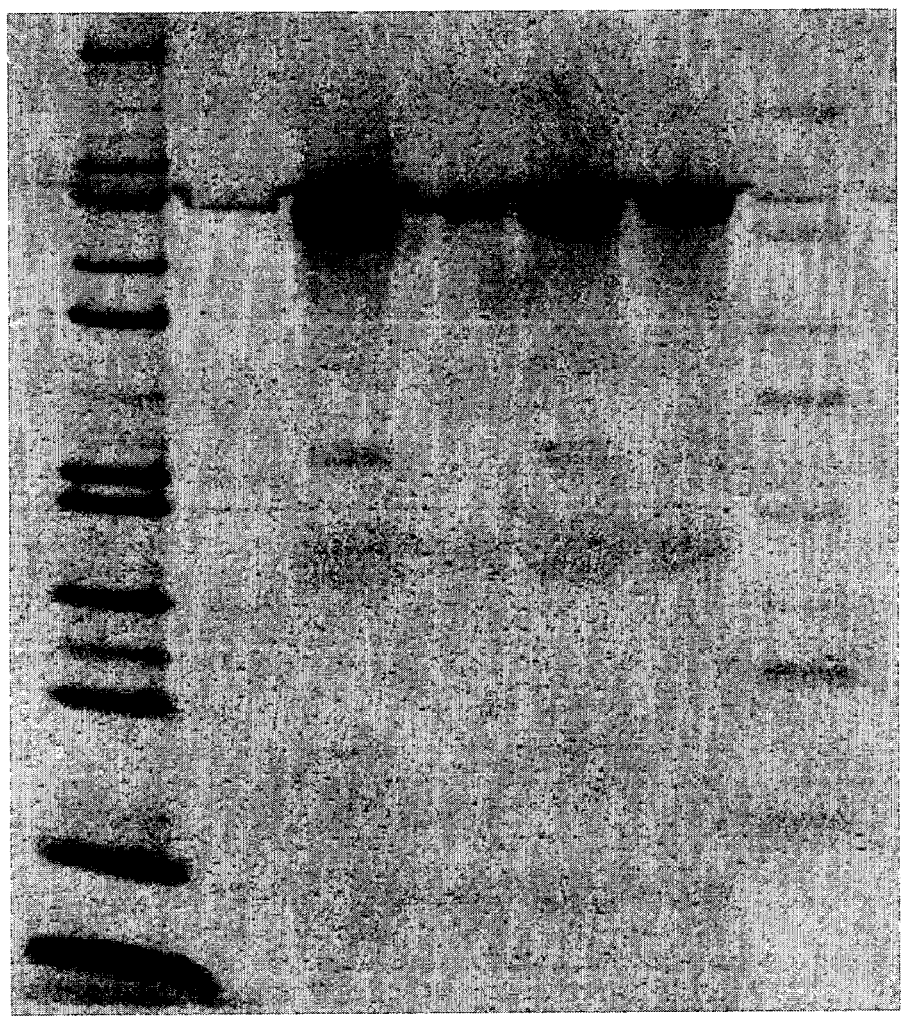

BtgZI Figure 4
Amino-terminal amino acid sequence of the BtgZI endonuclease:

M Y W L L D Y V T Q Q K V R N D I N N L I K X I L X I

TYPE II RESTRICTION ENDONUCLEASE BTGZI, OBTAINABLE FROM *BACILLUS THERMOGLUCOSIDASIUS* 36A AND A PROCESS FOR PRODUCING THE SAME

BACKGROUND OF THE INVENTION

The present invention relates to a novel Type II restriction endonuclease, BtgZI, obtainable from *Bacillus thermoglucosidasius* 36A (NEB#1384), and to a process for producing the same.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. The majority of restriction endonucleases recognize sequences of 4 to 6 nucleotides in length, although recently a small number of restriction endonucleases which recognize 7 or 8 uniquely specified nucleotides have been isolated. Most recognition sequences contain a dyad axis of symmetry and in most cases all the nucleotides are uniquely specified. However, some restriciton endonucleases have degenerate or relaxed specificities in that they recognize multiple bases at one or more positions in their recognition sequence, and some restriction endonucleases recognize asymmetric sequences. HaeIII, which recognizes the sequence 5'-GGCC-3', is an example of a restriction endonuclease having a symmetrical, non-degenerate recognition sequence, while HaeII, which recognizes 5'-(Pu)GCGC(Py)-3' typifies restriction endonucleases having a degenerate or relaxed recognition sequence. Endonucleases with symmetrical recognition sequences generally cleave symmetrically within or adjacent to the recognition site, while those that recognize asymmetric sequences tend to cleave at a distance of from 1 to 18 nucleotides away from the recognition site. More than two hundred unique restriction endonucleases have been identified among several thousands of bacterial species that have been examined to date.

Endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences 5'-(W)GGCC(W)-3', 5'-(Pu)GCGC(Py)-3' and 5'-GGCC-3' respectively. *Escherichia coli* RY13, on the other hand, synthesizes only one enzyme, EcoRI, which recognizes the sequence 5'-GAATTC-3'.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecule and cleaving them in each place that the recognition sequence occurs. The disintegration that results inactivates many of the infecting genes and renders the DNA susceptible to further degradation by exonucleases.

A second component of restriction systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always modified, by virtue of the activity of its modification methylase and it is therefore insensitive to the presence of the endogenous restriction endonuclease. It is only unmodified, and therefore identifiably foreign, DNA that is sensitive to restriction endonuclease recognition and attack. More than 3000 restriction endonucleases have been isolated from various bacterial strains. Of these, more than 200 recognize unique sequences, while the rest share common recognition specificities. Restriction endonucleases which recognize the same nucleotide sequence are termed "isoschizomers." Although the recognition sequences of isoschizomers are the same, they may vary with respect to site of cleavage (e.g., XmaI v. SmaI, Endow, et al., *J. Mol. Biol.* 112:521 (1977); Waalwijk, et al., *Nucleic Acids Res.* 5:3231 (1978)) and in cleavage rate at various sites (XhoI v. PaeR7I, Gingeras, et al., *Proc. Natl. Acad. Sci. U.S.A.* 80:402 (1983)).

There is a continuing need for novel type II restriction endonucleases. Although type II restriction endonucleases which recognize a number of specific nucleotide sequences are currently available, new restriction endonucleases which recognize novel sequences provide greater opportunities and ability for genetic manipulation. Each new unique endonuclease enables scientists to precisely cleave DNA at new positions within the DNA molecule, with all the opportunities this offers.

SUMMARY OF THE INVENTION

In accordance with the present invention, there is provided a novel restriction endonuclease obtainable from *Bacillus thermoglucosidasius* 36A (NEB#1384), hereinafter referred to as "BtgZI", which endonuclease:

(1) recognizes the nucleotide sequence 5'-GCGATG-3' in a double-stranded DNA molecule as shown below,

```
5'-GCGATGN10↓ -3'

3'-CGCTACN14↑-5'
```

(wherein G represents guanine, C represents cytosine, A represents adenine, T represents thymine and N represents either G, C, A, or T);

(2) cleaves said sequence in the phosphodiester bonds between the 10th and 11th nucleotide 3' to the recognition sequence 5'-GCGATG-3' on this strand and between the 14th and 15th nucleotides 5' to the recognition sequence of the complement strand 5'-CATCGC-3' to produce a four base 5' extension as indicated with the arrows; and (3) cleaves double-stranded pBR322 DNA to produce 3 fragments, the sizes of which are 2892 base pairs, 1181 base pairs and 288 base pairs.

The present invention further relates to a process for the production of the novel restriction endonuclease BtgZI. This process comprises either culturing *Bacillus thermoglucosidasius* 36A under conditions suitable for expressing BtgZI, collecting the cultured cells, obtaining a cell-free extract therefrom and separating and collecting the restriction endonuclease BtgZI from the cell-free extract, or culturing a transformed host, such as *E. coli*, containing the genes for the BtgZI methylase and endonuclease, collecting the cultured cells, obtaining a cell-free extract therefrom and separating and collecting the restriction endonuclease BtgZI from the cell-free extract.

BRIEF DESCRIPTION OF THE FIGURES

FIG. 1—Agarose gel showing BtgZI cleavage of lambda, T7, pBR322 and PhiX174 DNAs. Lanes 1, 4, 10 and 16: lambda-HindIII, PhiX174-HaeIII size standards; lane 2: lambda DNA+BtgZI; lane 3: T7 DNA+BtgZI; lane 5: pBR322 DNA+BtgZI+ClaI; lane 6: pBR322 DNA+BtgZI+NruI; lane 7: pBR322 DNA+BtgZI+NdeI; lane 8: pBR322 DNA+BtgZI+PstI; lane 9: pBR322 DNA+BtgZI; lane 11: PhiX174 DNA+BtgZI+PstI; lane 12: PhiX174 DNA+BtgZI+ SspI; lane 13: PhiX174 DNA+BtgZI+NciI; lane 14: PhiX174 DNA+btgZI+StuI; lane 15: PhiX174 DNA+BtgZI.

FIG. 2—Determination of the BtgZI cleavage site.

FIG. 2A shows the location of cleavage on 5'CATCGC-3' strand (SEQ ID NO:1, SEQ ID NO:2, and SEQ ID NO:3).

FIG. 2B shows the location of cleavage on 5'GCGATG strand (SEQ ID NO:4, SEQ ID NO:5, SEQ ID NO:6 and SEQ ID NO:7)

FIG. 3—SDS-PAGE gel of purified BtgZI endonuclease protein. Lanes 1 and 7: protein size standard (Novex); lanes 2, 3, 4, 5, and 6: BtgZI from Resource S column, fraction #15

FIG. 4—Amino-terminal amino acid sequence (SEQ ID NO:8) of the BtgZI endonuclease protein.

DETAILED DESCRIPTION OF THE INVENTION

The recognition sequence of the endonuclease of the present invention may be determined by mapping the locations of several BtgZI cleavage sites in various DNAs and comparing the DNA sequences of these regions for homology, then comparing the predicted cleavage fragments of the putative recognition sequence with the observed restriction fragments produced by BtgZI cleavage of various DNAs. The endonuclease BtgZI was found to cleave PhiX174 DNA twice, producing fragments of approximately 4950 bp and 450 bp. The location of these cut sites were mapped to approximate positions of 4450 and 4900 by simultaneously digesting PhiX174 DNA with BtgZI and with endonucleases which cleave at known positions, such as SspI, NciI, StuI and PstI (FIG. 1). Cut sites for BtgZI were similarly mapped in pBR322 DNA. The approximate size of the DNA fragments produced by BtgZI digestion of PhiX174 DNA and pBR322 DNA were entered into the program SITES (Gingeras, et al., *Nucl. Acids Res.* 5:4105 (1978)), which generates potential recognition sequences for the input data by comparing the fragment sizes which would result from cleavage of the DNA at any given recognition pattern with the input fragment sizes. One such potential pattern generated was 5'-GCGATG-3', which occurs in PhiX174 DNA at positions consistent with the mapping data obtained, i.e. at positions 4426 and 4896. This sequence also occurs in pBR322 DNA at positions consistent with the mapping data and the fragment sizes produced by BtgZI digestion of pBR322. The size of fragments predicted for cleavage at 5'-GCGATG-3' sites in PhiX174, pBR322, pUC19, T7 and lambda DNAs matched the observed size of fragments from cleavage of these DNAs with BtgZI, from which we conclude that BtgZI recognizes the sequence 5'-GCGATG-3'.

The point of cleavage within the BtgZI recognition sequence may be determined through dideoxy sequencing analysis of the terminal base sequence obtained from BtgZI cleavage of a suitable DNA substrate (Sanger, et al., *PNAS* 74:5463–5467 (1977) Brown, et al., *J. Mol. Biol.* 140: 143–148 (1980)). By the above referenced method (FIG. 2, exemplified in Example II) it was found that BtgZI cleaves the phosphodiester bond between the 10th and the 11th nucleotides 3' to the recognition sequence in the 5'-GCGATG-3 strand of the DNA, and between the 14th and 15th nucleotides 5' to the recognition sequence in the complement stand, 5'-CATCGC- 3', to produce a 4 base 5' extension, as indicated by the arrows:

```
5'-GCGATGNNNNNNNNNNN↓-3'         (SEQ ID NO:9)

3'-CGCATGNNNNNNNNNNNNNN↑-5'
```

In accordance with the present invention, BtgZI is obtained by culturing *Bacillus thermoglucosidasius* 36A and recovering the endonuclease from the cells. A sample of *Bacillus thermoglucosidasius* 36A (NEB#1384) has been deposited under the terms and conditions of the Budapest Treaty with the American Type Culture Collection (ATCC) on Jun. 25, 2003, and bears the Patent Accession No. PTA-5292.

For recovering the enzyme of the present invention *Bacillus thermoglucosidasius* 36A (NEB#1384) may be grown using any suitable technique. For example, *Bacillus thermoglucosidasius* 36A may be grown in Luria broth media (BBL Microbiology Systems, Cockeysville, Md.) incubated aerobically at 55° C. Cells in the late logarithmic stage of growth are collected by centrifugation and either disrupted immediately or stored frozen at −70° C.

The BtgZI enzyme can be isolated from *Bacillus thermoglucosidasius* 36A cells by conventional protein purification techniques. For example, cell paste is suspended in a buffer solution and treated by sonication, high pressure dispersion or enzymatic digestion to allow extraction of the endonuclease by the buffer solution. Intact cells and cellular debris are then removed by centrifugation to produce a cell-free extract containing BtgZI. The BtgZI endonuclease is then purified from the cell-free extract by ion-exchange chromatography, affinity chromatography, molecular sieve chromatography, or a combination of these methods to produce the endonuclease of the present invention.

The endonuclease of the present invention along with its corresponding methylase may also be obtained using recombinant DNA techniques, such as the methylation selection technique disclosed in U.S. Pat. No. 5,200,333. As an example, DNA from a bacterial strain which contains an R-M system, such as *Bacillus thermoglucosidasius* 36A, is purified, partially digested with suitable type II endonucleases, and ligated to an appropriate cleaved, dephosphorylated cloning vector. The ligated DNA is transformed into an appropriate host, such as *E. coli*, the transformants are pooled and the population of recombinant DNA molecules are purified to form libraries. The library of clones is then challenged by digesting with an endonuclease which will selectively destroy vectors which do not contain and express the methylase of the R-M system being cloned. Vectors which contain and express the methylase gene of interest will be modified at the endonuclease recognition sites of the challenging endonuclease and thus be immune from cleavage. The challenged clone pools are then transformed back into the appropriate host to recover the undigested, presumably methylase expressing clones. The transformants may be screened for endonuclease activity or cycled through further rounds of purification and selection. Finally, individual transformants are selected and their DNA purified. These clones are analyzed for resistance to cleavage by the endonuclease of interest and for common insert DNA. Cell extracts prepared from transformants which demonstrate endonuclease resistance are assayed in vitro for methyltransferase and endonuclease activities.

The present invention is further illustrated by the following Examples. These Examples are provided to aid in the understanding of the invention and are not construed as a limitation thereof.

The references cited above and below are herein incorporated by reference.

EXAMPLE I

Production of BtgZI Endonuclease

*Bacillus thermoglucosidasius* 36A strain NEB#1384 was grown in Rich media (10 g Peptone, 5 g Yeast Extract, 5 g NaCl per liter.). The cells were incubated aerobically at 55° C. until late logarithmic stage (20 hours). The cells were then harvested by centrifugation and stored frozen at −70° C.

248 grams of the cells obtained above were suspended in 744 mls buffer A (20 mM Tris-HCl, 0.1 mM EDTA, 10 mM beta-mercaptoethanol, 5% glycerol, pH 8.0 at 25 C) adjusted to 250 mM NaCl. The cells were lysed by four passes through a Gaulin press at 3000 psi, releasing approximately 50 mg of protein per gram of cells. The cell lysate was clarified by centrifugation at 15000×g by batch in a Sharples centrifuge. 1000 mls of supernatant was obtained containing approximately 11 g of soluble protein.

The supernatant solution was applied to a 500 ml DEAE Fast-Flow column (Amersham Biosciences, Piscataway N.J.) equilibrated in Buffer A adjusted to 250 mM NaCl. A 700 ml wash of Buffer A adjusted to 250 mM NaCl was applied. The effluent from the applied supernatant and wash were pooled and diluted to 125 mM NaCl using Buffer A.

The diluted pool was applied to a 500 ml Heparin Hyper-D column (Biosepra, Marlborough Mass.) equilibrated with Buffer A adjusted to 125 mM NaCl. A 500 ml wash of buffer A adjusted to 125 mM NaCl was applied and then a 1900 ml linear NaCl grandient from 125 mM NaCl to 600 mM NaCl in buffer A was applied to the Heparin Hyper-D column and fractions of 25 ml were collected. Fractions were assayed for BtgZI activity by incubation with 1 μg of Lambda DNA in 1× NEBuffer 4 for fifteen minutes at 60° C. BtgZI activity eluted at 480 mM to 530 mM NaCl.

The Heparin Hyper-D column fractions containing the BtgZI activity were pooled, diluted to 50 mM NaCl in Buffer A and applied to a 300 ml S.P. Sepharose Fast Flow column (Amersham Biosciences, Piscataway N.J.). A 500 ml wash of buffer A adjusted to 50 mM NaCl was applied, then a 2200 ml linear gradient of NaCl from 50 mM NaCl to 500 mM NaCl in buffer A was applied and 25 ml fractions were collected. The BtgZI activity eluted between 300 mM NaCl and 340 mM NaCl.

The S.P. Sepharose Fast Flow column fractions containing the BtgZI activity were pooled, diluted to 100 mM NaCl in Buffer A and applied to a 50 ml P11/D1225 column (Whatman, Clifton N.J.). A 100 ml wash of buffer A adjusted to 100 mM NaCl was applied, then a 460 ml linear gradient of NaCl from 100 mM NaCl to 600 mM NaCl in buffer A was applied and 5 ml fractions were collected. The BtgZI activity eluted between 420 mM NaCl and 470 mM NaCl.

The P11 column fractions containing the BtgZI activity were pooled, dialyzed against Buffer A adjusted to 100 mM NaCl and applied to a 20 ml Q-Sepharose HP column (Amersham Biosciences, Piscataway N.J.). A 20 ml wash of buffer A adjusted to 100 mM NaCl was applied. The BtgZI activity was found in the flow-through.

The Q-sepharose flow-through pool was applied to an 8 ml Heparin TSK column (TosoHaas). A 16 ml wash of buffer A adjusted to 100 mM NaCl was applied, then a 160 ml linear gradient of NaCl from 100 mM NaCl to 600 mM NaCl in buffer A was applied and 2 ml fractions were collected. The BtgZI activity eluted between 350 mM NaCl and 380 mM NaCl.

The Heparin TSK column fractions containing the BtgZI activity were pooled, dialyzed against Buffer A adjusted to 50 mM NaCl and applied to a 6 ml Resource S column. (Amersham Biosciences). A 12 ml wash of Buffer A adjusted to 50 mM NaCl was applied, then a 120 ml linear gradient of NaCl from 100 mM NaCl to 600 mM NaCl in buffer A was applied and 2 ml fractions were collected. The BtgZI activity eluted between 220 mM NaCl and 260 mM NaCl and contained approximately 45,000 units of activity. The BtgZI was substantially pure and free of contaminating endonuclease and exonuclease activities.

The purified BtgZI was applied to an SDS-PAGE 4% to 20% gradient Polyacrylamide gel (ICN Biomedicals, Aurora Ohio). The BtgZI endonuclease was observed to migrate as a single band with an apparent molecular weight of approximately 95 kiloDaltons (FIG. 3), as determined by comparison to protein size standards, Mark12 Wide Range Protein Standard (Novex).

Bovine serum albumin was added as a stabilizer to a final concentration of 200 μg/ml and the BtgZI enzyme was dialyzed against storage buffer (50% glycerol, 50 mm NaCl, 10 mM Tris-HCl, 0.1 mM Dithiothreitol, pH 7.4) and was stored at −20 C.

Activity Determination

BtgZI activity: Samples of from 1 to 10 μls were added to 50 μls of substrate solution consisting of 1× NEBuffer 4 containing 1 μg Lambda phage DNA supplemented with 100 μg/ml BSA. The reaction was incubated at 60° C. for 60 minutes. The reaction was terminated by adding 20 μl of Stop Solution (50% glycerol, 50 mM EDTA pH 8.0, and 0.02% Bromophenol Blue). The reaction mixture was applied to a 1% agarose gel and electrophoresed. The bands obtained were identified by comparison with DNA size standards.

Unit Definition: One unit of BtgZI is defined as the amount of BtgZI required to completely cleave 1 microgram of Lambda DNA in a total reaction volume of 50 μl 1× NEBuffer 4, supplemented with 100 g/ml BSA (bovine serum albumin) within one hour at 60° C.

Enzyme Properties:

Temperature:

BtgZI exhibits a temperature optimum near 60° C., as determined by a one hour incubation in 1× NEBuffer 4 supplemented with 100 μg/ml BSA. Incubation at 37° C. for one hour results in an activity of approximately 30%, relative to the activity at 60° C. Incubation at 65° C. for one hour results in 40% of the cutting at 60° C. Incubation at 70° C. for one hour results in 35% of the cutting at 60° C.

SAM:

Supplementing the BtgZI reaction with 20 μM SAM (S-adenosyl-methionine) did not appreciably effect the activity of BtgZI.

BSA:

Supplementing the BtgZI reaction in 1× NEBuffer 4 at 60° C. with BSA to a final concentration of 100 μg/ml increased BtgZI activity by approximately 100% relative to the same reaction conditions without BSA present.

Activity in Various Reaction Buffers:

BtgZI was found to be most active in NEBuffer 4+BSA, relative to other standard NEBuffers. Digestion for at 60° C. for one hour in the following NEBuffers yielded the following approximate percentage cleavage relative to NEBuffer 4+BSA:

NEBuffer 1+BSA–10%
NEBuffer 2+BSA–25%
NEBuffer 3+BSA–<5%
NEBuffer EcoRI+BSA–<5%
NEBuffer BstYI+BSA–10%
NEBuffer NruI+BSA–50%

Activity in a 16 hour reaction:

When incubated at either 37° C. or 60° C., BtgZI did not show an increase in activity in a 16 hour digest relative to a one hour digest.

EXAMPLE II

Determination of The BtgZI Cleavage Site

The location of BtgZI cleavage relative to the recognition sequence was determined by cleaving a suitable DNA molecule and then performing DNA sequencing from a suitable primer to the end of the cleaved DNA template. A plasmid DNA, pSEP.S3AI8.G10, consisting of a fragment of DNA isolated from an environmental sample inserted into the vector pUC19, into which the GPS2.1 transprimer (New England Biolabs) had been inserted, was employed as the template. This template was chosen because there were BtgZI sites in opposite orientations conveniently located at approximately 150 base pairs from the "North" priming site and 295 bases from the "South" priming site of the GPS system. Any sequenceable DNA that has a BtgZI site within several hundred base pairs of a priming site will work for this analysis, however, such as pBR322 DNA, if a suitable primer is available or is synthesized. The pSep.S3AI8.G10 plasmid DNA was cleaved with BtgZI by combining:

20 μl 10× NEBuffer #4
20 μl pSEP.S3AI8.G10 DNA (5 μg)
160 μl dH$_2$O
2 μl BtgZI (8 units)

and incubating for 1 hour at 37° C. The cleaved DNA was purified and concentrated using a Qiagen Qiaprep DNA spin column according to the manufacturer's instructions. The DNA was eluted in a volume of 50 μl.

Sequencing Reactions

The sequencing reactions were performed using an ABI377 DNA sequencer according to the manufacturer's instructions, using the cleaved pSEP.S3AI8.G10 DNA and either the GPS "North" or the GPS "South" primer:

```
GPS "North"
                                           (SEQ ID NO:10)
5'-ACTTTATTGTCATAGTTTAGATCTATTTTG-3'

GPS "South"
                                           (SEQ ID NO:11)
5'-ATAATCCTTAAAAACTCCATTTCCACCCCT-3'
```

The results indicate BtgZI cleaves DNA between the 10th and the 11th nucleotides 3' to the recognition sequence in the 5'-GCGATG-3' strand of the DNA, and between the 14th and 15th nucleotides 5' to the recognition sequence in the complement stand, 5'-CATCGC-3', to produce a 4 base 5' extension (FIG. 2).

EXAMPLE III

Determination of the BtgZI Amino Terminal Amino Acid Sequence

Amino acid sequences of the BtgZI endonuclease were obtained from the amino terminus of the BtgZI polypeptide. The BtgZI restriction endonuclease, prepared as described in example I above, was subjected to electrophoresis and electroblotted according to the procedure of Matsudaira (Matsudaira, P., J. Biol. Chem. 262:10035–10038, 1987), with modifications as previously described (Looney, et al., Gene 80:193–208 (1989)). The membrane was stained with Coomassie blue R-250 and the protein band of approximately 95 kDa (FIG. 3) was excised and subjected to sequential degradation on an ABI Procise 494 Protein/Peptide Sequencer with gas-phase delivery (Waite-Rees, et al., J. Bacteriol. 173:5207–5219 (1991)). The amino acid sequence of the first 27 amino terminal residues obtained was the following: M Y W L L D Y V T Q Q K V R N D I N N L I K X I L X I (SEQ ID NO:8).

SEQUENCE LISTING

<160> NUMBER OF SEQ ID NOS: 11

<210> SEQ ID NO 1
<211> LENGTH: 39
<212> TYPE: DNA
<213> ORGANISM: Bacillus thermoglucosidasius

<400> SEQUENCE: 1
cgatgagaat gcgatgttgg tggccaaaag caattatcc                    39

```
<210> SEQ ID NO 2
<211> LENGTH: 26
<212> TYPE: DNA
<213> ORGANISM: unknown
<220> FEATURE:
<223> OTHER INFORMATION: resulting cleaved DNA of SEQ ID NO:1

<400> SEQUENCE: 2
cgatgagaat gcgatgttgg tggcca                                26

<210> SEQ ID NO 3
<211> LENGTH: 26
<212> TYPE: DNA
<213> ORGANISM: unknown
<220> FEATURE:
<223> OTHER INFORMATION: primer annealed and extended through BtgZI
      site and adds extra (A) base

<400> SEQUENCE: 3
agaatgcgat gttggtggcc aaaaga                                26

<210> SEQ ID NO 4
<211> LENGTH: 45
<212> TYPE: DNA
<213> ORGANISM: Bacillus thermoglucosidasius

<400> SEQUENCE: 4
ttctttctgc gcggtcaact ttgtaccaat catacatcgc ctgag           45

<210> SEQ ID NO 5
<211> LENGTH: 20
<212> TYPE: DNA
<213> ORGANISM: unknown
<220> FEATURE:
<223> OTHER INFORMATION: resulting cleaved DNA of SEQ ID NO:4

<400> SEQUENCE: 5
ttctttctgc gcggtcaact                                       20

<210> SEQ ID NO 6
<211> LENGTH: 25
<212> TYPE: DNA
<213> ORGANISM: unknown
<220> FEATURE:
<223> OTHER INFORMATION: resulting cleaved DNA of SEQ ID NO:4

<400> SEQUENCE: 6
ttgtaccaat catacatcgc ctgag                                 25

<210> SEQ ID NO 7
<211> LENGTH: 25
<212> TYPE: DNA
<213> ORGANISM: unknown
<220> FEATURE:
<223> OTHER INFORMATION: Primer annealed and extended through the BtgZI
      site

<400> SEQUENCE: 7
ttctttctgc gcggtcaact ttgta                                 25

<210> SEQ ID NO 8
<211> LENGTH: 27
<212> TYPE: PRT
<213> ORGANISM: unknown
<220> FEATURE:
<223> OTHER INFORMATION: first 27 amino acids
```

-continued

```
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid

<400> SEQUENCE: 8

Met Tyr Trp Leu Leu Asp Tyr Val Thr Gln Gln Lys Val Arg Asn Asp
1               5                   10                  15

Ile Asn Asn Leu Ile Lys Xaa Ile Leu Xaa Ile
            20                  25

<210> SEQ ID NO 9
<211> LENGTH: 16
<212> TYPE: DNA
<213> ORGANISM: unknown
<220> FEATURE:
<223> OTHER INFORMATION: BtgZI cleaves the phosphodiester bond between
      the 10th and 11th nucleotides 3' to the recognition sequence in
      5'-GCGATG3' strand of the DNA and between the 14th and 15th
      nucleotices in the complement strand to produce the 4-base
      extension
<220> FEATURE:
<221> NAME/KEY: misc_feature
<222> LOCATION: (7)..(16)
<223> OTHER INFORMATION: n is a, c, g, or t

<400> SEQUENCE: 9
gcgatgnnnn nnnnnn                                                   16

<210> SEQ ID NO 10
<211> LENGTH: 30
<212> TYPE: DNA
<213> ORGANISM: unknown
<220> FEATURE:
<223> OTHER INFORMATION: GPS North Primer

<400> SEQUENCE: 10
actttattgt catagtttag atctattttg                                    30

<210> SEQ ID NO 11
<211> LENGTH: 30
<212> TYPE: DNA
<213> ORGANISM: unknown
<220> FEATURE:
<223> OTHER INFORMATION: GPS South Primer

<400> SEQUENCE: 11
ataatcctta aaaactccat ttccacccct                                    30
```

What is claimed is:

1. A substantially pure Type II restriction endonuclease obtainable from *Bacillus thermoglucosidasius* 36 A (ATCC Accession No. PTA-6692) recognizing the following base sequence in double-stranded deoxyribonucleic acid molecules:

```
5'-GCGATGNNNNNNNNNN↓-3'      (SEQ ID NO:9)

3'-CGCTACNNNNNNNNNNNNNN↑-5'
``` and having a cleavage position defined by the arrows.

2. A method for obtaining the Type II restriction endonuclease of claim 1, comprising cultivating a sample of *Bacillus thermoglucosidasius* 36A under conditions favoring the production of said endonuclease and separating said endonuclease therefrom.

3. The Type II restriction endonuclease of claim 1, wherein the restriction endonuclease is purified from *Bacillus thermoglucosidasius* 36A (ATCC Accession No. PTA-5292).

* * * * *

UNITED STATES PATENT AND TRADEMARK OFFICE
CERTIFICATE OF CORRECTION

| | |
|---|---|
| PATENT NO. | : 7,029,900 B2 |
| APPLICATION NO. | : 10/617361 |
| DATED | : April 18, 2006 |
| INVENTOR(S) | : Richard D. Morgan et al. |

It is certified that error appears in the above-identified patent and that said Letters Patent is hereby corrected as shown below:

At column 6, line number 58, delete "g/ml" and insert -- µg/ml --, therefor.

Signed and Sealed this
Tenth Day of May, 2011

David J. Kappos
*Director of the United States Patent and Trademark Office*